United States Patent
Zuhaib et al.

(10) Patent No.: US 10,500,305 B2
(45) Date of Patent: Dec. 10, 2019

(54) DEVICE AND METHOD FOR A NANOFIBER WRAP TO MINIMIZE INFLAMATION AND SCARRING

(71) Applicant: THE JOHNS HOPKINS UNIVERSITY, Baltimore, MD (US)

(72) Inventors: Ibrahim Zuhaib, Balitmore, MD (US); Hai-Quan Mao, Balitmore, MD (US); Kellin Krick, Baltimore, MD (US); Russell Martin, Balitmore, MD (US); Gerald Brandacher, Balitmore, MD (US); Karim A. Sarhane, Baltimore, MD (US)

( * ) Notice: Subject to any disclaimer, the term of this patent is extended or adjusted under 35 U.S.C. 154(b) by 248 days.

(21) Appl. No.: 15/128,257

(22) PCT Filed: Apr. 9, 2015

(86) PCT No.: PCT/US2015/025031
§ 371 (c)(1),
(2) Date: Sep. 22, 2016

(87) PCT Pub. No.: WO2015/157485
PCT Pub. Date: Oct. 15, 2015

(65) Prior Publication Data
US 2017/0095591 A1    Apr. 6, 2017

Related U.S. Application Data

(60) Provisional application No. 61/977,881, filed on Apr. 10, 2014.

(51) Int. Cl.
*A61L 27/18* (2006.01)
*A61L 27/50* (2006.01)
(Continued)

(52) U.S. Cl.
CPC ............... *A61L 27/18* (2013.01); *A61L 27/26* (2013.01); *A61L 27/50* (2013.01); *A61L 27/56* (2013.01);
(Continued)

(58) Field of Classification Search
CPC ........... A61L 27/28; A61L 27/56; A61L 27/26
(Continued)

(56) References Cited

U.S. PATENT DOCUMENTS

| 6,080,192 A | 6/2000 | Demopulos et al. |
| 7,993,412 B2 | 8/2011 | Webster et al. |

(Continued)

OTHER PUBLICATIONS

Sarhane, Karim A.; Selectively Permeable Nanofiber Constructs to Prevent Inflammatory Scarring and Enhance Nerve Regeneration in Peripheral Nerve Injury; Mar. 2014; Plastic and Reconstructive Surgery; vol. 133, No. 3; pp. 16-17 (Year: 2014).*

(Continued)

*Primary Examiner* — Tahseen Khan
(74) *Attorney, Agent, or Firm* — Casimir Jones, S.C.; Jeffrey W. Childers

(57) ABSTRACT

The present invention is directed to a device and method for a nanofiber wrap to minimize inflation and scarring of nerve tissue and maximize the nutrient transport. More particularly, the present invention is directed to a novel semi-permeable nanofiber construct prepared from biocompatible materials. The nanofiber construct is applied around a nerve repair site following end-to-end anastomosis. The nanofiber construct is porous and composed of randomly oriented nanofibers prepare using an electrospinning method. The nanofiber construct has a wall that is approximately 50-100 µm thick with pores smaller than 25 µm. The nanofiber construct prevents inflammatory cells from migrating into the nerve coaption site, while still permitting the diffusion of growth factors and essential nutrients. The nanofiber con- (Continued)

struct allows for enhanced neuroregeneration and optimal function outcomes.

9 Claims, 11 Drawing Sheets

(51) Int. Cl.
*A61L 27/26* (2006.01)
*A61L 27/56* (2006.01)
*D01D 5/00* (2006.01)
*D01F 8/14* (2006.01)

(52) U.S. Cl.
CPC ............... *D01D 5/003* (2013.01); *D01F 8/14* (2013.01); *A61L 2400/12* (2013.01); *A61L 2430/32* (2013.01); *D10B 2509/00* (2013.01)

(58) Field of Classification Search
USPC ......................................................... 428/220
See application file for complete search history.

(56) References Cited

U.S. PATENT DOCUMENTS

| | | |
|---|---|---|
| 2008/0233162 A1 | 9/2008 | Lee et al. |
| 2010/0310623 A1* | 12/2010 | Laurencin ................. A61F 2/28 424/423 |
| 2010/0331980 A1* | 12/2010 | Lee .......................... A61L 27/26 623/14.13 |
| 2011/0125170 A1* | 5/2011 | Hoke ................. A61B 17/1128 606/152 |
| 2012/0068384 A1* | 3/2012 | Phaneuf ............... A61K 9/0092 264/466 |
| 2013/0230601 A1* | 9/2013 | Itskovitz-Eldor .... C12N 5/0662 424/572 |
| 2015/0023911 A1* | 1/2015 | Schilling ................ A61K 38/00 424/85.2 |
| 2015/0354094 A1* | 12/2015 | Parker ...................... D01D 5/18 428/221 |

OTHER PUBLICATIONS

Sarhane, K. A. et al. "Selectively Permeable Nanofiber Constructs to Prevent Inflammatory Scarring and Enhance Nerve Regeneration in Peripheral Nerve Injury" Plastic & Reconstructive Surgery, Mar. 7, 2014, vol. 133, No. 3S, pp. 16-17.

* cited by examiner

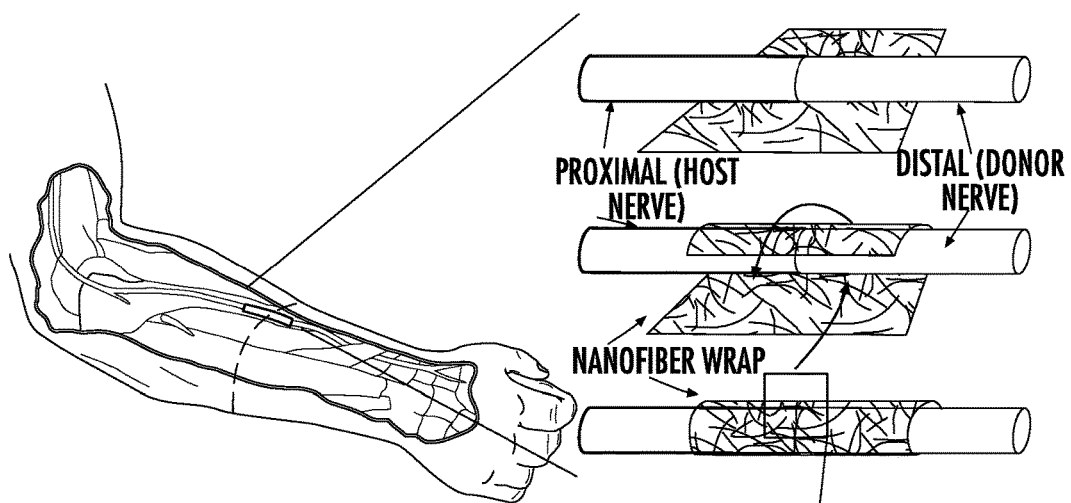
FIG. 3A
FIG. 3B
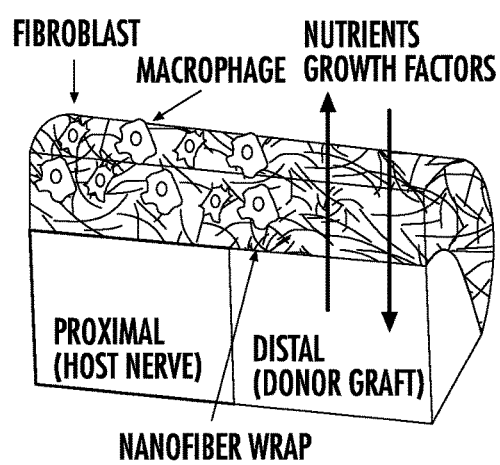
FIG. 3C

| | GROUP | INTERVENTION | ENDPOINT |
|---|---|---|---|
| EARLY MEASURES OF NERVE REGENERATION (SCARRING/INFLAMMATION ASSESSMENT) | 1 | SCIATIC TRANSECTION AND REPAIR | WEEK 5 |
| | 2 | SCIATIC TRANSECTION AND REPAIR + NERVE WRAP | WEEK 5 |
| LONG-TERM MEASURES OF NERVE REGENERATION (FUNCTIONAL OUTCOME ASSESSMENT) | 3 | SCIATIC TRANSECTION AND REPAIR | WEEK 16 |
| | 4 | SCIATIC TRANSECTION AND REPAIR + NERVE WRAP | WEEK 16 |

*FIG. 5*

MASSON'S TRICHROME STAINING
CONTROL    EXPERIMENTAL

IMMUNOFLUORESCENCE CO-STAINING
CONTROL    EXPERIMENTAL

CONTROL EXPERIMENTAL

GASTROCNEMIUS MUSCLE LAMININ IMMUNOFLUORESCENCE
CONTROL                    EXPERIMENTAL

FIG. 11A                   FIG. 11B

DEVICE AND METHOD FOR A NANOFIBER WRAP TO MINIMIZE INFLAMATION AND SCARRING

CROSS-REFERENCE TO RELATED APPLICATIONS

This application is a 35 U.S.C. § 371 U.S. national entry of International Application PCT/US2015/025031, having an international filing date of Apr. 9, 2015, which claims the benefit of U.S. Provisional Application No. 61/977,881, filed Apr. 10, 2014, the content of each of the aforementioned applications is herein incorporated by reference in their entirety.

FIELD OF THE INVENTION

The present invention relates generally to medical devices. More particularly, the present invention relates to a device and method for a nanofiber wrap to minimize inflammation and scarring of nerve and other tissues as well as any other tubular structure or as a layered constituent of a biologic or synthetic mesh.

BACKGROUND OF THE INVENTION

Peripheral nerve injuries constitute a frequent and disabling condition, with an estimated incidence of 23 out of every 100,000 persons per year in developed countries. This statistic does not account for non-traumatic cases (i.e. nerve damage secondary to abdominal or pelvic surgeries) and for lesions not treated at health facilities. Despite great advances in microsurgical techniques, nerve repair continues to be suboptimal, and full functional recovery is seldom achieved. There is thus an imminent need to develop novel strategies to enhance neuroregeneration and optimize return of function.

Research in peripheral nerve injuries has shown that the formation of scar and fibrosis at the site of nerve coaptation impedes axonal regeneration. Furthermore, a negative correlation between the degree of functional recovery and the amount of scar formation at the repair site is a well-established phenomenon. Although nerve regeneration normally occurs at the rate of 1 to 3 mm per day, regenerating axons may require up to 20 to 40 days to traverse the scar at the site of nerve repair. Reduction in scar formation at a site of nerve repair is associated with better recovery. Mechanistically, scarring at the nerve repair site is due to invasion of inflammatory cells, with subsequent upregulation of fibrogenic cytokines.

It would therefore be beneficial to provide an inert barrier around the coaptation site that prevents inflammatory cells infiltration while still allowing diffusion of nutrients and other growth factors to promoting nerve regeneration.

SUMMARY OF THE INVENTION

The foregoing needs are met, to a great extent, by the present invention, which provides a device for promoting healing at a connection site between tubular biologic structures including a construct of nanofibers. The nanofibers are spun from a biocompatible material in a sheet configured and sized for wrapping around the connection site tubular biologic structures. The sheet is configured to have a pore size to prevent the infiltration of inflammatory cells to the connection site.

In accordance with an aspect of the present invention, the sheet is approximately 50 µm to 500 µm thick. More particularly the sheet can have a thickness of approximately 100 µm. The device can have pore size of approximately 0.5-25 µm. The biocompatible material can be polyester, such as polycaprolactone, polylactide, or polyglycolide. The biocompatible material can also be a blend of synthetic polyester such as polycaprolactone and a natural macromolecule such as collagen. Each one of the nanofibers can have a diameter of approximately 100 nm to 25 µm. The nanofibers are formed using a system comprising a syringe, a source of voltage, and a copper plate. While a copper plate is described herein with respect to the preferred embodiment any sort of conductive plate or rod known to or conceivable by one of skill in the art could also be used. A needle of the syringe has a gauge of approximately 27, a distance between the source of voltage and the copper plate of approximately 6 cm, an applied voltage from the source of voltage of approximately 7.5 kV, and a flow rate of solution from the syringe of approximately 0.75 mL/h.

In accordance with an aspect of the present invention, a method for forming a device for promoting healing at a connection site between tubular biologic structures includes filling a syringe with a solution containing a biocompatible material for forming the nanofibers. The method includes applying an electrical current to the solution containing the biocompatible material, such that the solution extends out into a fiber. Additionally, the method includes extruding the solution onto a grounded plate in an electrospinning process until a predetermined thickness of a sheet of the fiber, such that the sheet has a pore size of less than 10 µm.

In accordance with yet another aspect of the present invention, the method further includes using the solution comprising an 8 wt % PCL (MW=80,000) solution in a 9:1 (by wt) ratio of dichloromethane:N, N-dimethylformamide. The method includes using the biocompatible material taking the form of a polyester. Additionally, the method includes using one selected from a group consisting of a polycaprolactone, polylactide, and polyglycolide. The method includes using the biocompatible material formed from a blend of synthetic polyester such as polycaprolactone and a natural macromolecule such as collagen. The method also includes using the grounded plate comprising a conductive material.

In accordance with still another aspect of the present invention, the method includes using a grounded plate with dimensions of approximately 11 cm×11 cm×0.3 cm. The method includes using a power supply for applying the electrical current to the solution. The method includes forming the fiber having a diameter of approximately 100 nm to 10 µm and forming the sheet with a thickness of approximately 50 µm to approximately 500 µm. The method includes forming the sheet using a flow rate of 0.75 mL/h; a distance between applied voltage and the grounded plate of 6 cm; an applied voltage of 7.5 kV; and a needle gauge of 27. Additionally, the method includes applying the method for one consisting of a group of repairing one selected from a group consisting of crushed, compressed, and injured peripheral and cranial nerves and protecting one selected from a group consisting of autologous and allogeneic nerve grafts. The method also includes repairing injured or inflamed tendons.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIGS. 3A-3C illustrate schematic diagrams of a nanofiber wrap according to an embodiment of the present invention.

FIG. 5 illustrates a summary of the Groups, the intervention used, and the endpoint.

FIGS. 11A-11D illustrate image and graphical views of gastrocnemius muscle weight and laminin staining analysis.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to a device and method for a nanofiber wrap to minimize inflation and scarring of nerve tissue as well as any other cylindrical structures, such as a tendon, a ligament, or a vessel, or as a layered constituent of a biologic or synthetic mesh to cover a wound repair site. More particularly, the present invention is directed to a novel-semi permeable nanofiber construct prepared from biocompatible materials. The nanofiber construct is wrapped around a nerve repair site. The nanofiber construct is porous and composed of randomly oriented nanofibers prepared using an electrospinning technique. The nanofiber construct has a wall that is approximately 100 µm thick with pores smaller than 25 µm. The nanofiber construct prevents inflammatory cells from migrating into the nerve coaption site, while still permitting the diffusion of growth factors and essential nutrients. The nanofiber construct allows for enhanced neuroregeneration and optimal function outcomes.

Figure 1:
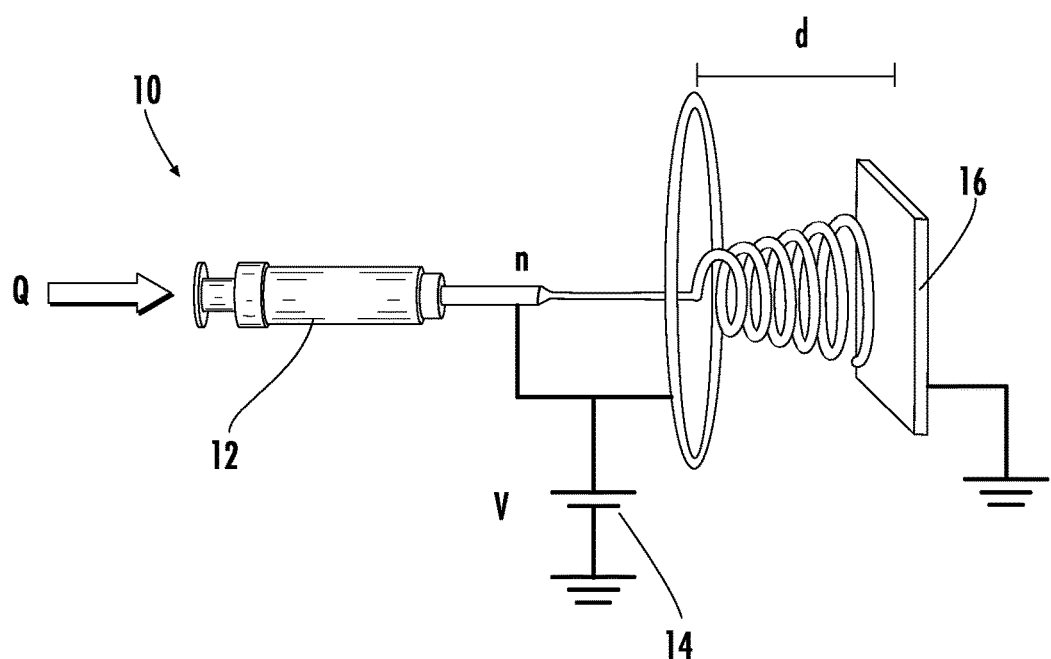
FIG. 1 illustrates an exemplary setup for fabricating an electrospun nanofiber wrap according to an embodiment of the present invention.

FIG. 1 illustrates an exemplary setup for fabricating an electrospun nanofiber construct wrap according to an embodiment of the present invention. The exemplary setup 10 for fabricating the electrospun nanofiber construct wrap includes a syringe 12 containing a solution containing a biocompatible material for forming the nanofibers. In a preferred embodiment, the solution can take the form of an 8 wt % PCL (MW=80,000) solution in a 9:1 (by wt) ratio of dichloromethane:N, N-dimethylformamide. The biocompatible material can take the form of a polyester, such as polycaprolactone, polylactide, or polyglycolide. The biocompatible material can also be a blend of synthetic polyester such as polycaprolactone and a natural macromolecule such as collagen. It should be noted that these examples are not meant to be considered limiting and any suitable material known to or conceivable by one of skill in the art can be used. The exemplary setup also includes a power supply 14 and a square, grounded copper plate 16. While a copper plate is described herein with respect to a preferred embodiment any sort of conductive plate or rod known to or conceivable by one of skill in the art could also be used. It can also be a rod or other curved surface for giving the nanofiber wrap some initial curl. The copper plate 16 can be in any suitable size known to or conceivable by one of skill in the art for this purpose. However, in an exemplary embodiment the plate is approximately 11 cm×11 cm×0.3 cm. The solution is extruded from the syringe onto the copper plate and nanofibers are formed through the process of electrospinning and applying a current to the solution, which causes it to stretch out into a fiber shape. The exemplary setup includes several variable elements including, but not limited to, flow rate (Q), distance between applied voltage and the copper plate (d), applied voltage (V), and needle gauge (n). These variables can be adjusted to change the properties of the nanofibers produced by the exemplary setup 10. For instance, according to an embodiment of the invention the nanofibers can be produced under the following conditions: Q=0.75 mL/h; d=6 cm; V=7.5 kV; and n=27. With this exemplary setup constructs of 100 µm thick with pores smaller than 10 µm are obtained. The thickness of the nanofiber wrap can range from 50 to 500 µm. While this exemplary setup is described herein, any suitable setup known to or conceivable by one of skill in the art could also be used. Generally, the nanofibers produced using the exemplary setup have a diameter of approximately 100 nm to 10 µm. However, any suitable length or diameter known to or conceivable by one of skill in the art could also be used.

Figure 2A:
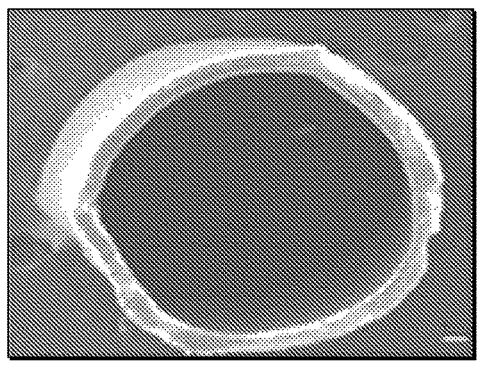
FIGS. 2A-2D illustrate images of an exemplary nanofiber wrap according to an embodiment of the present invention.
Figure 2B:
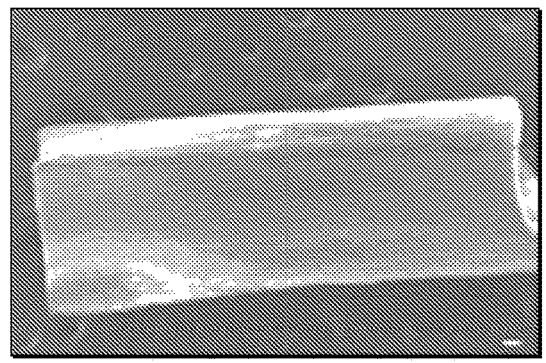
Figure 2C:
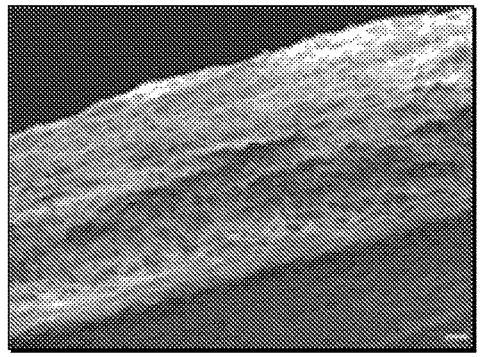
Figure 2D:
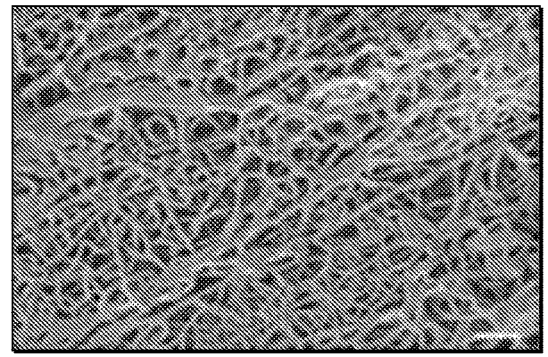

FIGS. 2A-2D illustrate images of an exemplary nanofiber wrap according to an embodiment of the present invention. As illustrated in FIGS. 2A-2D the nanofiber wrap has a thickness of 100 µm and a pore size of less than 10 µm. FIG. 2A illustrates a cross section of a nanofiber wrap according to the present invention. FIG. 2B illustrates a side view of a nanofiber wrap according to an embodiment of the present invention. FIG. 2C illustrates a cross section of a wall of the nanofiber wrap and FIG. 2D illustrates porosity of the nanofiber wrap.

FIGS. 3A-3C illustrate schematic diagrams of a nanofiber wrap according to an embodiment of the present invention. FIG. 3A illustrates a nanofiber wrap according to the present invention, as placed in an arm of a patient. FIG. 3B illustrates a schematic diagram of a nanofiber wrap according to the present invention being wrapped around a nerve repair site. As illustrated in FIG. 3B, the wrap is placed at the nerve repair site, and more particularly at a joint of the host nerve and the donor nerve. The wrap is placed around the joint and secured with a fixative, such as a drop of fibronectin glue or sutures. FIG. 3C illustrates a sectional schematic view of the wrap placed around the joint of the nerve repair site. The macroporous nanofiber mesh restricts the infiltration of macrophages and fibroblasts to the nerve repair site, while the access of nutrients, growth factors, and oxygen, in general are enabled. The trapped macrophages can also be tuned from an inflammatory phenotype to a pro-healing phenotype (more indicative of M2 phenotype than M1 phenotype), thus rendering the local environment pro-regenerative.

EXAMPLE

An exemplary implementation is described herein. This description is merely illustrative and is not meant to be considered limiting. Thy-1 GFP transgenic rats, whose axons constitutively express GFP, were used for the example. Four groups in total were used; 2 for short-term assessment of nerve regeneration measures (Groups 1 and 2) and 2 others for long-term assessment (Groups 3 and 4).

Figures 4A, 4B:
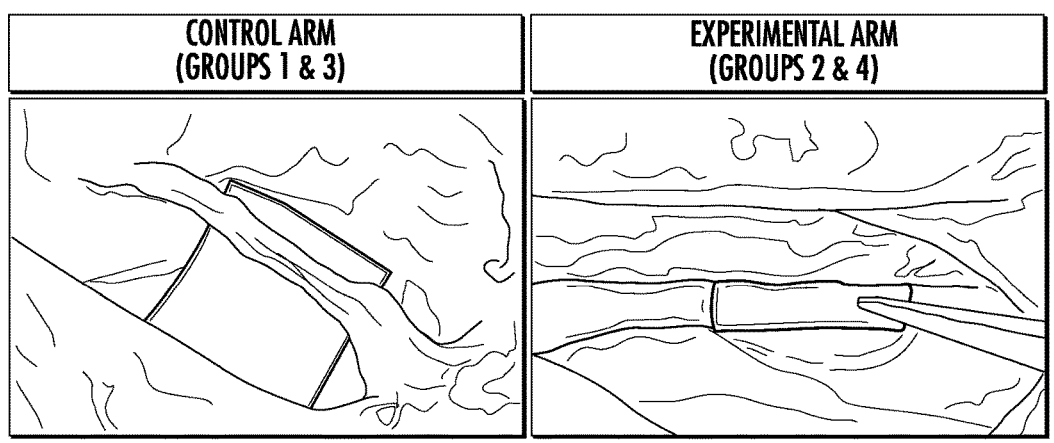
FIGS. 4A and 4B illustrate an exemplary rat arm or leg nerve to be wrapped with the nanofiber construct for Groups 1 and 3 and an exemplary rat arm nerve to be wrapped with the nanofiber construct for Groups 2 and 4, respectively.

In Group 1 (control short-term group), a sciatic nerve transection and epineureal repair was performed; in Group 2 (experimental short-term group), in addition to sciatic transection and epineureal repair, the repair site was wrapped with the nanofiber construct. Groups 1 and 2 were harvested at 5 weeks for assessment of nerve inflammation/fibrosis. Groups 3 and 4, consisting of control and experimental long-term groups, respectively, were harvested at 16 weeks for assessment of nerve and muscle functional recovery. FIGS. 4A and 4B illustrate an exemplary rat arm nerve to be wrapped with the nanofiber construct for Groups 1 and 3 and an exemplary rat arm nerve to be wrapped with the nanofiber construct for Groups 2 and 4, respectively. FIG. 5, illustrates a summary of the Groups, the intervention used, and the endpoint.

Early measures of nerve regeneration (at 5 weeks following implantation) consisted of inflammation/scarring quantification at the repair site; collagen deposition was assessed by Masson's Trichrome staining; macrophage invasion was evaluated by co-immunofluorescent staining (CD68/TUJ1 staining); and inflammatory cytokine gene expression was assessed by qRT-PCR. Additionally, the number of regenerated myelinated axons was quantified at this early time point by analyzing the histomorphometric measures of nerve cross sections taken 5 mm distal.

Late measures of nerve regeneration (16 weeks) consisted of neuromuscular junction (Sciatic nerve—Soleus muscle) re-innervation quantification ($\alpha$-Bungarotoxin/GFP staining), muscle histology assessment (gastrocnemius muscle weight and laminin staining), as well as serial electrophysiological measurements starting week 8 (every 2 weeks until week 16). The compound motor action potentials (CMAPs) were measured in the re-innervated intrinsic foot muscles in the plantar surface using subdermal needle electrodes. Stimulation was accomplished by subdermal needle electrodes placed near the sciatic nerve at the sciatic notch.

Figure 6A:
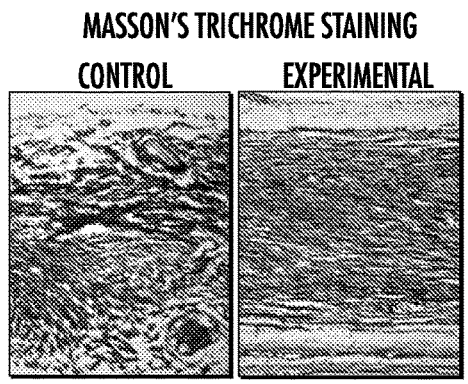
FIGS. 6A-6D illustrate images and graphical views of the percent of collagen at the repair site and the macrophage counts at the repair site.
Figure 6C:
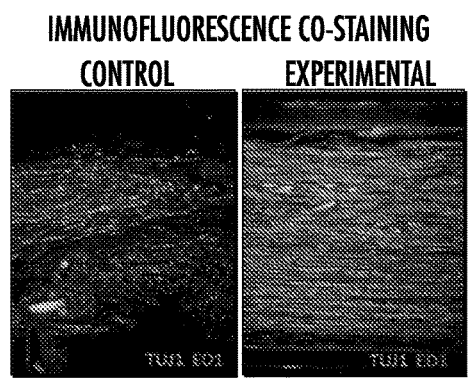
Figure 6B:
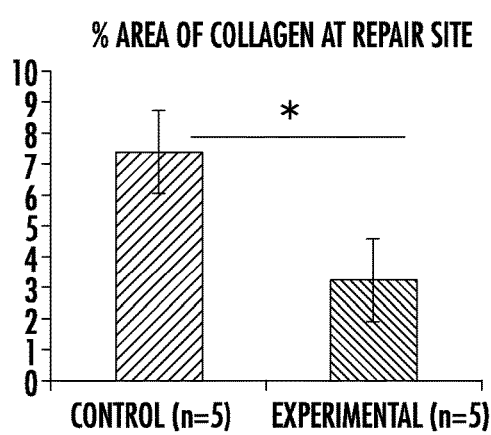
Figure 6D:
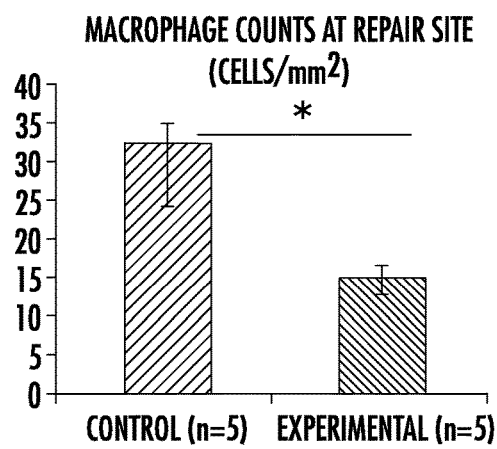

Masson's Trichrome and double immunofluorescence staining (ED1+TUJ1) of nerve longitudinal sections 5 weeks following repair showed a significantly decreased level of intraneural scarring and inflammation in the nanofiber nerve wrap group, as determined by collagen quantification (7.4%±1.3 vs. 3.2%±1.3, $p<0.05$) and macrophage counting (32.2±2.4 cells/mm$^2$ vs. 14.6±1.8 cells/mm$^2$, $p<0.05$) in the repair site (n=5/group). Collagen was trapped outside the nerve wrap in the experimental group, as illustrated in FIGS. 6A and 6B). FIGS. 6A-6D illustrate images and graphical views of the percent of collagen at the repair site and the macrophage counts at the repair site. As illustrated in FIGS. 6A and 6B, the percentage area of Masson's Trichrome blue staining for collagen was quantified at the coaptation site. As illustrated in FIGS. 6C and 6D, intraneural macrophage (positive for ED-1) were counted at the coaptation site, and results are expressed as cells/mm$^2$ (10 µm sections, 40× mag). ED-1 (CD68): Macrophage marker TUJ1 (Neuronal Class III $\beta$-Tubulin): Neurofilament marker.

Figure 7:
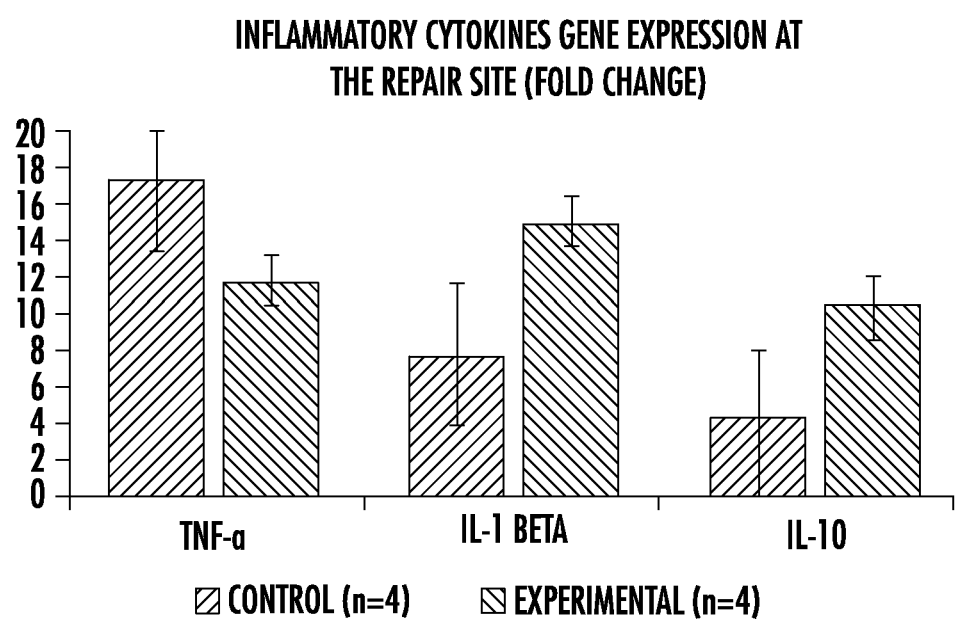
FIG. 7 illustrates a graphical view of up-regulation of the anti-inflammatory cytokine IL-10 and down-regulation of the pro-inflammatory cytokine TNF-α that were detected at the nerve repair site in the experimental group.

Mechanistically, these outcomes were correlated to an up-regulation of the anti-inflammatory cytokine (IL-10) and down-regulation of the pro-inflammatory cytokine (TNF-$\alpha$). FIG. 7 illustrates a graphical view of up-regulation of the anti-inflammatory cytokine IL-10 and down-regulation of the pro-inflammatory cytokine TNF-$\alpha$ were detected at the nerve repair site in the experimental group. Furthermore, nerve cross sections taken 5 mm distal to the coaptation site demonstrated a significantly increased number of myelinated axons in the experimental group (n=8 per group) (FIGS. 6A-6D).

Figure 8A:
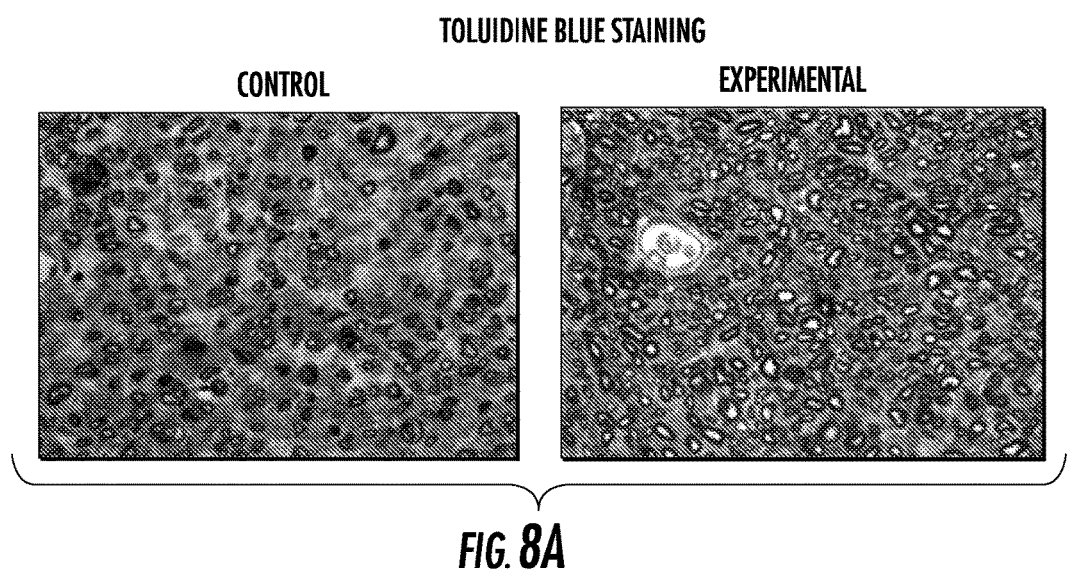
FIGS. 8A and 8B illustrate images of nerve cross sections for the control and experimental groups as well as a graphical view of regenerated myelinated axons in the experimental and control groups.
Figure 8B:
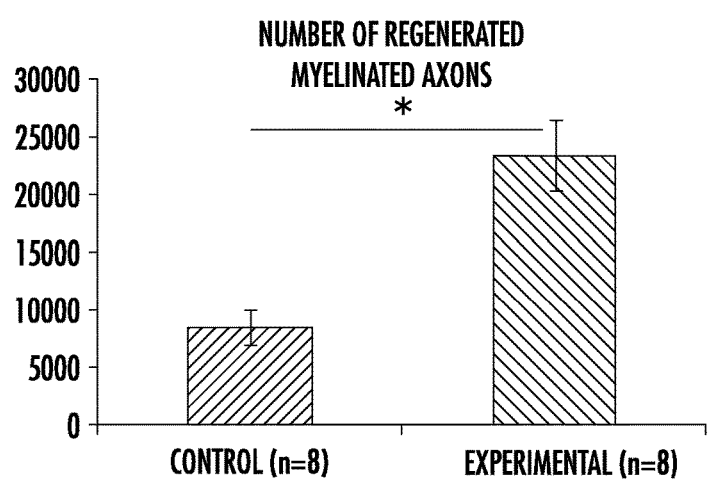

FIGS. 8A and 8B illustrate images of nerve cross sections for the control and experimental groups as well as a graphical view of regenerated myelinated axons in the experimental and control groups. As illustrated in FIGS. 8A-8B, numbers of regenerated myelinated axons were counted at 5 mm distal to the repair site (ultra-thin sections, 1000× mag).

Figure 9:
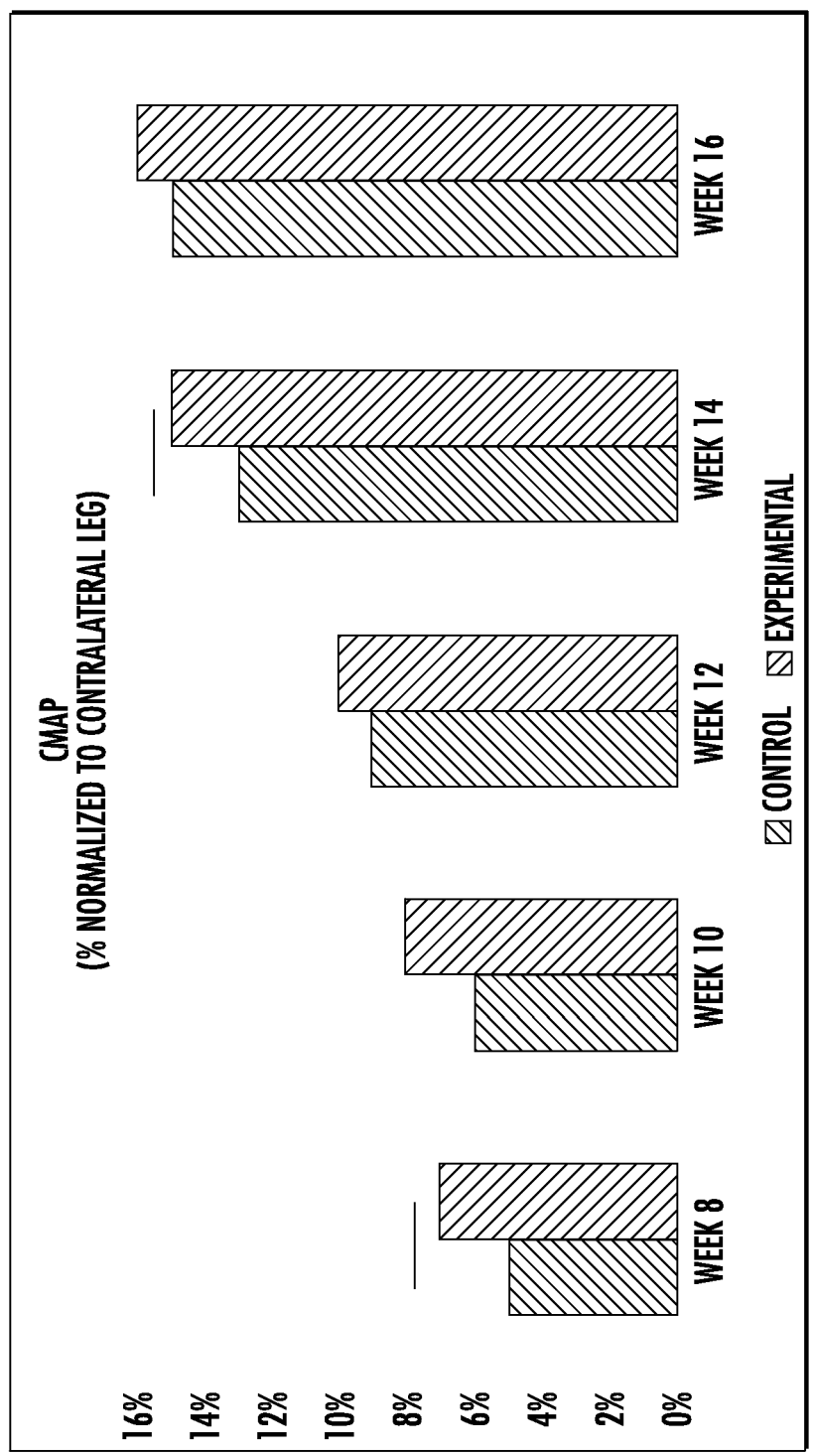
FIG. 9 illustrates a graphical view of serial electrophysiological measurements showing improved functional recovery in the experimental group.

Electrophysiological measurements showed return of function at week 8 with significantly higher CMAPs in the experimental group. This trend persisted throughout week 16. Furthermore, the number of re-innervated neuromuscular junctions was significantly higher in the experimental group. FIG. 9 illustrates a graphical view of serial electrophysiological measurements showing improved functional recovery in the experimental group.

Figure 10A:
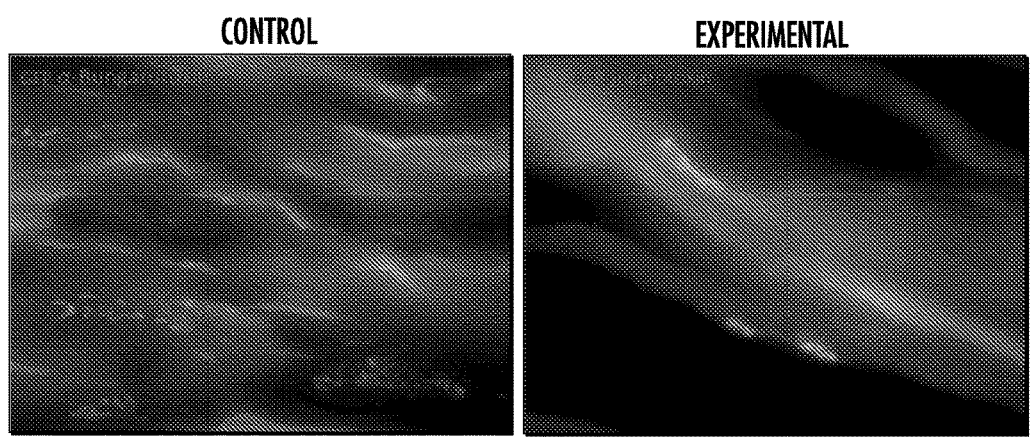
FIGS. 10A and 10B illustrate images of neuromuscular junction and a graphical view of neuromuscular junction re-innervation quantification. Increased reinnervation in the experimental group was accompanied by decreased gastrocnemius muscle atrophy, as assessed by a higher muscle weight and higher single muscle fiber cross sectional area.
Figure 10B:
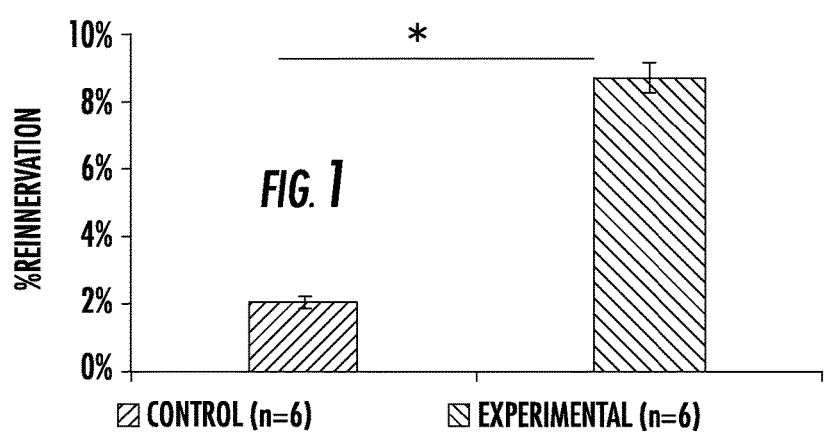
Figure 11C:
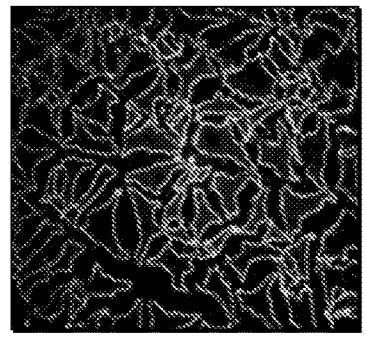
Figure 11C:
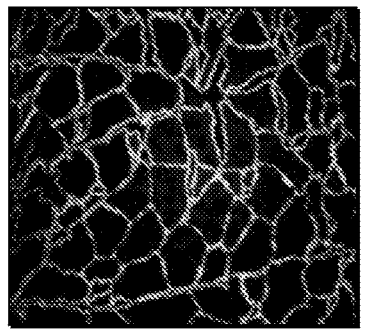
Figure 11C:
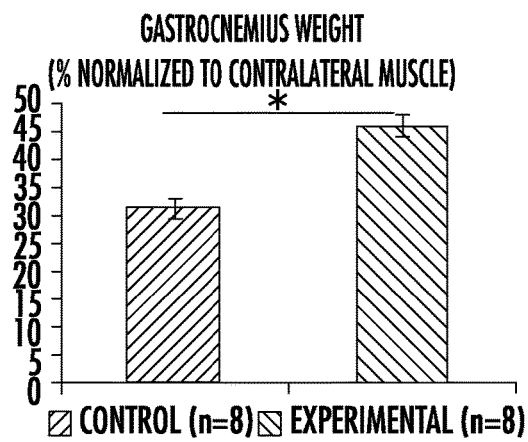
Figure 11D:
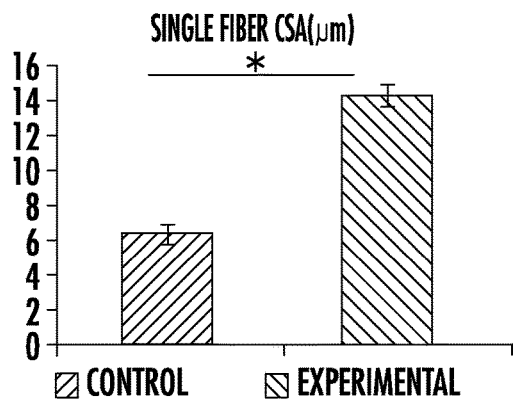

FIGS. 10A and 10B illustrate images of neuromuscular joints and a graphical view of neuromuscular junction re-innervation quantification. Increased reinnervation in the experimental group was accompanied by decreased gastrocnemius muscle atrophy, as assessed by a higher muscle weight and higher single muscle fiber cross sectional area. FIGS. 11A-11C illustrate image and graphical views of gastrocnemius muscle weight and laminin staining analysis.

These results effectively demonstrated decrease inflammatory response and connective tissue proliferation at the site of neurorrhaphy and improved nerve regeneration with optimal functional outcomes. While the invention is described above with respect to nerve tissue, the invention can also be applied to vessels or any other generally tubular structure. Therefore, the nanofiber wrap design is optimized for minimizing scarring at a connection site between two tubular structures such as nerves or vessels. It can also potentially prevent pain from neuroma formation. The construct can also be applied to blood vessel anastomosis by preventing leakage of blood cells at connection sites.

The many features and advantages of the invention are apparent from the detailed specification, and thus, it is intended by the appended claims to cover all such features and advantages of the invention, which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A device for promoting healing at a connection site between tubular biologic structures comprising:
   a porous, semipermeable construct of nanofibers;
   wherein the nanofibers are spun from a biocompatible material in a sheet configured and sized for wrapping around the connection site tubular biologic structures; and
   wherein the sheet is configured to have a pore size to entrap inflammatory cells and prevent infiltration of inflammatory cells to the connection site, while permitting nutrient supply.

2. The device of claim 1 further comprising the sheet being approximately 50 µm to 500 µm thick.

3. The device of claim 1 further comprising the sheet being approximately 100 µm thick.

4. The device of claim 1 further comprising the pore size of approximately 0.5-25 µm.

5. The device of claim 1 wherein the biocompatible material comprises one selected from a group consisting of polycaprolactone, polylactide, or polyglycolide.

6. The device of claim 1 wherein the biocompatible material comprises a polymer blend of polycaprolactone and collagen.

7. The device of claim 1 further comprising each one of the nanofibers having a diameter of approximately 100 nm to 10 µm.

8. The device of claim 1 wherein the nanofibers are formed by electrospinning method.

9. The device of claim 8 wherein a needle of the syringe has a gauge of approximately 27, a distance between the source of voltage and a conductive material of approximately 6 cm, an applied voltage from the source of voltage of approximately 7.5 kV, and a flow rate of solution from the syringe of approximately 0.75 mL/h.

* * * * *

UNITED STATES PATENT AND TRADEMARK OFFICE
CERTIFICATE OF CORRECTION

PATENT NO. : 10,500,305 B2
APPLICATION NO. : 15/128257
DATED : December 10, 2019
INVENTOR(S) : Zuhaib Ibrahim et al.

Page 1 of 1

It is certified that error appears in the above-identified patent and that said Letters Patent is hereby corrected as shown below:

On the Title Page

Item (72) should read:
(72) Inventors: Zuhaib Ibrahim, Baltimore, MD (US);
Hai-Quan Mao, Baltimore, MD (US);
Kellin Krick, Baltimore, MD (US);
Russell Martin, Baltimore, MD (US);
Gerald Brandacher, Baltimore, MD (US);
Karim A. Sarhane, Baltimore, MD (US)

Signed and Sealed this
Ninth Day of June, 2020

Andrei Iancu
*Director of the United States Patent and Trademark Office*